United States Patent [19]

Kenmochi

[11] Patent Number: 4,833,910
[45] Date of Patent: May 30, 1989

[54] METHOD FOR RESIN MOLDING MONITORING

[75] Inventor: Kazuei Kenmochi, Hirakata, Japan

[73] Assignee: Matsushita Electric Industrial Co., Ltd., Osaka, Japan

[21] Appl. No.: 946,403

[22] Filed: Dec. 19, 1986

[30] Foreign Application Priority Data

Dec. 19, 1985 [JP] Japan ................. 60-286064

[51] Int. Cl.⁴ ............................................. G01N 11/04
[52] U.S. Cl. .................................. 73/56; 264/40.3; 425/149
[58] Field of Search ............... 264/40.1, 40.7, 40.3, 264/40.5; 73/55, 56, 54, 714, 753, 861.42, 861.43; 425/135, 145, 146, 149, 155, 159, 162

[56] References Cited

U.S. PATENT DOCUMENTS

| | | | |
|---|---|---|---|
| 3,860,801 | 1/1975 | Hunkar | 425/145 |
| 4,241,602 | 12/1980 | Han et al. | 73/56 |
| 4,644,781 | 2/1987 | Mon | 73/54 |

FOREIGN PATENT DOCUMENTS

| | | |
|---|---|---|
| 48-73457 | 10/1973 | Japan . |
| 56-7862 | 2/1981 | Japan . |
| 60-46008 | 10/1985 | Japan . |

Primary Examiner—Jan H. Silbaugh
Assistant Examiner—Jill L. Heitbrink
Attorney, Agent, or Firm—Wenderoth, Lind & Ponack

[57] ABSTRACT

A lever pivoted at a support point receives force from pressure receiving members located at two positions along the direction of flow of resin in a flow passage without a metal mold. A physical property or condition of the resin flowed into the metal mold is determined as a function of the time during which the resin flows between the two pressure receiving members and of a difference pressure acting on the lever at the two positions.

6 Claims, 4 Drawing Sheets

METHOD FOR RESIN MOLDING MONITORING

BACKGROUND OF THE INVENTION

The present invention relates to a method of monitoring the molding process of resin molding within a metal mold.

Molding of resin by using a metal mold is extremely common, including injection molding, transfer molding, compression molding, or the like. Such operations flow, fill and harden the resin in a cavity within the metal mold to form moldings. Particularly, in injection molding and transfer molding, the resin is caused to flow through a narrow area, which is called sprue, runner, gate or the like.

Roughly speaking, it is easy to repeatedly produce moldings of precise size, surface shape, strength or the like during such a resin molding operation. Thus, by filling constant quantities of material into a given shape of a metal mold cavity, and identical moldings always are produced. However, as the ranges of allowable tolerances of size, shape, strength and so on are reduced, it has become extremely difficult to repeatedly produce resin moldings with better precision.

This is why resin viscosity, repeating precision of the operation of the molding machine, the temperature of the metal mold have to be taken into consideration. However, the sequence of cause and effect of such factors is not explained in theory, but is explained through the accumulation of the respective actual examples.

Under such conditions, many proposals have been made of improving the accuracy of repetition in the production of moldings. Known detection systems chiefly are divided into two types. One system is to detect parameters of operating mechanisms, for example, screw speed, screw driving hydraulic pressure, screw revolution number, plunger speed and so on, while the other system is to detect parameters such as, for example, resin temperature, resin pressure, flow speed and so on, of the resin within the metal mold.

Action in response to such detected values also is divided into two types. One is to perform a feedback into the operation of the molding machine, while the other is to estimate the tolerance of the molding for a molding shot to determine quality.

The system of detecting parameters of the operation of the machine is easier to achieve feedback into the operation of the machine, but has a disadvantage that reproducibility is not strictly checked, because the action of the resin will be uncertain due to factors such as resin compressibility, friction with the machine, and so on.

The system of detecting parameters of the resin within the metal mold is advantageous because it is directly related to phenomena actually occurring within the mold.

A system of detecting the pressure within the metal mold is provided as one example of such system. The method described in Japanese Patent Publication (examined) No. 52-44346 detects the resin pressure near at the furthest portion within the metal mold from the inlet to control retention pressure. Also, in Japanese Laid-Open Patent Application (unexamined) No. 53-120769, resin pressures both near the sprue or gate and near the furthest portion from the inlet are detected, and a switch in pressure is detected when the pressure difference changes from decreasing to increasing during continuous measurement of such difference.

A system of detecting the speed of flow of resin flowing within a metal mold is another system. In Japanese Patent Publication (examined) No. 57-30658, two resin detectors are provided in a flow passage, and the speed of flow is detected by measurement of the time for flow between two points to perform a feedback operation into the molding conditions. In the method of Japanese Patent Publication (examined) No. 56-7862, several temperature sensing elements are disposed within the metal mold to detect the tip-end position, i.e., what is referred to as a melt front, of the resin flow to control the molding machine.

Though these mold interior detecting systems have the advantage of detecting actual operating conditions, they are slightly inferior with respect to repetition accuracy of the molding operation, so that the object of the detection operation cannot be sufficiently achieved. The correlation factor between the weight of a polyacetal molding of, for example, 2 mm in thickness, 45 mm in length and about 1 g in weight and the mold interior resin pressure was 0.07 in a normal molding machine. It is apparent that the effect is small if the pressure control of the molding machine is achieved with a pressure sensor provided within the mold in a case like this.

It has become obvious that the resin temperature and the resin viscosity greatly contribute towards the reproducibility of the moldings. Of course, as the background where such conclusion is drawn, the reliability of the mechanism of the molding machine is sufficiently increased at present, and the repetition accuracy of the control of the molding machine is improved. Also, it may be applied to a case where the repetition accuracy of the molding is expected to be further increased. It is found out that the correlation factor increases if the tolerance range of the mold interior pressure becomes larger.

A method of measuring the temperature and viscosity of the resin immediately before the filling operation into the metal mold located within the molding machine may be considered from the background described hereinabove. The method of Japanese Patent Publication (examined) No. 60-46008 measures the apparent viscosity of the resin from the screw action, for example, torque, to perform a feedback control of the molding conditions.

However, the viscosity of the resin is determined from the relation between the shearing speed and the temperature. The viscosity which is determined from the torque of the screw is not directly related to the viscosity of the resin flowing into the metal mold.

What is really required is the temperature, viscosity and shearing speed of the resin which starts to actually flow into the metal mold. These values are required to be detected a sufficient time before the resin is filled into the cavity of the mold.

Namely, in order to predict the tolerance range of the molding in the course of the molding process, the shearing speed which has an effect upon the viscosity of the resin flowing through a resin passage within the metal mold is obtained, and, furthermore, the resin temperature at such position is measured.

SUMMARY OF THE INVENTION

Accordingly, an object of the present invention is to provide a monitoring method comprising the steps of positioning pressure-receiving members at two locations facing the resin passage along the direction of flow of the resin within the metal mold, transferring the force acting on such two pressure receiving members to a lever which pivots in opposite directions, and detecting a physical property of the resin as a function of the pivoting over time of the lever in opposite directions.

Another object of the present invention is to provide a resin-molding monitoring apparatus comprising two pressure-receiving members facing the resin flow passage within the metal mold, a lever for supporting the pressure-receiving members at two locations so that the lever is rotatable in reverse directions about a support point in response to pressures acting on the two members sequentially, a converter for determining a physical property of the resin as a function of the amount of pivoting of the lever in the two opposite directions over time.

With the above arrangement, the force is applied to the pressure receiving member provided facing the resin flow passage when the molten resin flows through the resin flow passage or when the pressure is applied even if the flow of the molten resin stops. The lever receives the forces acting on the pressure receiving members located upon two places so that the lever pivots in opposite directions. When the two pressure receiving members are provided at equal distances from the support point of the lever, the pressure difference between the two points is employed by the converter to determine the physical property. If the distance between the support point of the lever and the two pressure receiving members is unequal, both the pressure difference between two points and an absolute pressure value may be detected.

The pressure difference between two points within the metal mold may be determined by one converting means. The time required for the resin to flow between the two points may be determined through a continuous sampling operation. The viscosity and the shearing speed of the resin may be obtained from the pressure difference, the time, the flow passage shape, and furthermore the resin temperature may be detected. Moldings which are stable in quality may be provided by electrically controlling the operation of a valve regulating the injection pressure or the injection speed in accordance with the results determined per the above.

BRIEF DESCRIPTION OF THE DRAWINGS

These and other objects and features of the present invention will become apparent from the following description taken in conjunction with preferred embodiment thereof with reference to the accompanying drawings, in which.

DETAILED DESCRIPTION OF THE INVENTION

Figure 1:
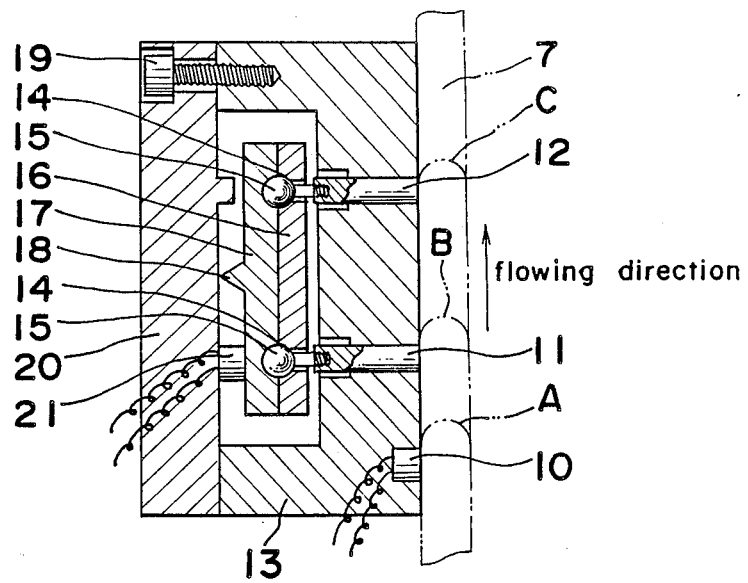
FIG. 1 is a cross-sectional view of a resin pressure detecting means in a first embodiment of the present invention.

Before the description of the present invention proceeds, it is to be noted that like parts are designated by like reference numerals throughout the accompanying drawings.

Figure 2:
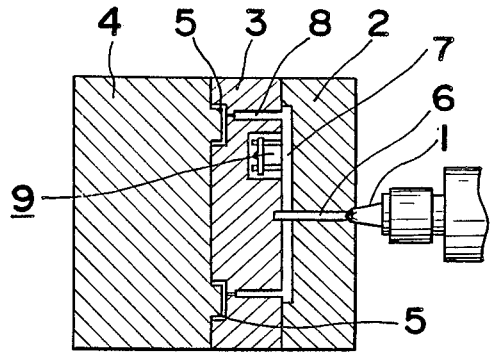
FIG. 2 is a cross-sectional view of a mold with the resin pressure detecting means of FIG. 1 being built-in therein.

Referring now to the drawings, there is shown in FIG. 2 a condition where the resin pressure detecting means in a first embodiment of the present invention is incorporated into a metal mold. Shown therein is a nozzle 1 which is one portion of injection means for injecting molten resin into the metal mold, a mold plate 2, a cavity plate 3, a core plate 4, cavities 5, sprue 6, a runner 7, second runners 8, and a resin pressure detecting means 9 built into the cavity plate 3.

FIG. 1 is a cross-sectional view showing on enlarged scale the resin pressure detecting means 9 in FIG. 2. A pressure sensor 10, a pressure receiving pin 11 and a pressure receiving pin 12 are provided in order in the flowing direction of the resin, facing the runner 7, within a case 13. The pressure receiving pins 11, 12, together with the case 13 are slidable in the axial direction. Screws 14 with ball-shaped head portions 15 are secured onto the ends of pins 12 and 11 opposite to the pressure receiving faces thereof. The head portion 15 of each screw 14 is grasped between plates 16, 17. A support point 18 located at the intermediate portion of the plate 17 contacts a bottom plate 20 that is secured with a bolt 19 to the case 13. A pressure sensor 21 contacts a side of plate 17 opposite to the fact thereof against which the ball-shaped head portion 14 comes into contact and at a position aligned with the pressure receiving pin 11. The distance between the support point 18 and the pressure receiving pin 11 or the pressure receiving pin 12 is almost equal. Also, the pressure receiving pins 11 and 12 are of equal diameter. The plate 17 operates as a lever, with the support point 18 as a center, and may swing thereabout within a restricted range. If the pressure sensor 21 or the bottom plate 20 are slightly deformed by the pressure applied to the pressure receiving pin, displacement may occur.

Figure 3:
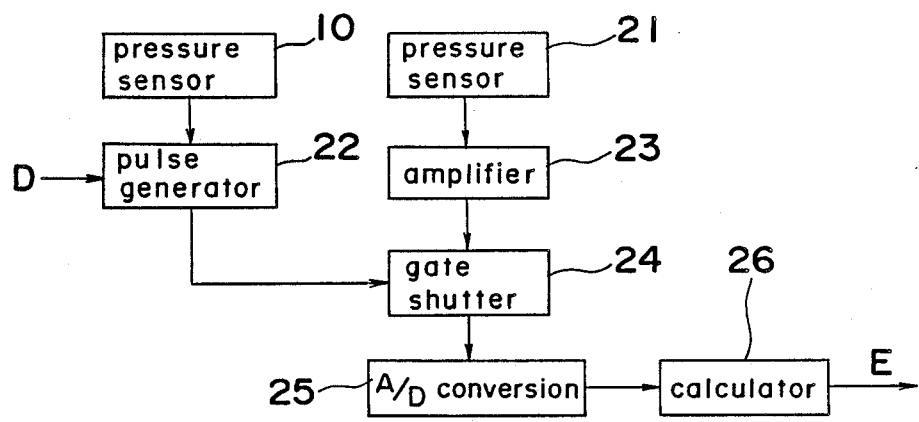
FIG. 3 is a block diagram of a circuit for processing the signals from a pressure sensor to be contained in the resin pressure detecting means.

FIG. 3 is a block diagram of a signal processing system including the pressure sensors of FIG. 1. When a small voltage is produced by the pressure sensor 10, a pulse generator 22 periodically generates pulses to feed them to a gate switch 24 before stop signals D are input. The voltage caused in the pressure sensor 21 is amplified by an amplifier 23, so that the voltage value and the pressure value are in a constant relationship with each other, and is fed to an A/D converter 25 through the gate switch 24. A signal digitalized by the A/D converter 25 passes to a calculator 26, and signals E based on a calculation thereby are output and are used as signals for controlling the injection process.

Figure 4:
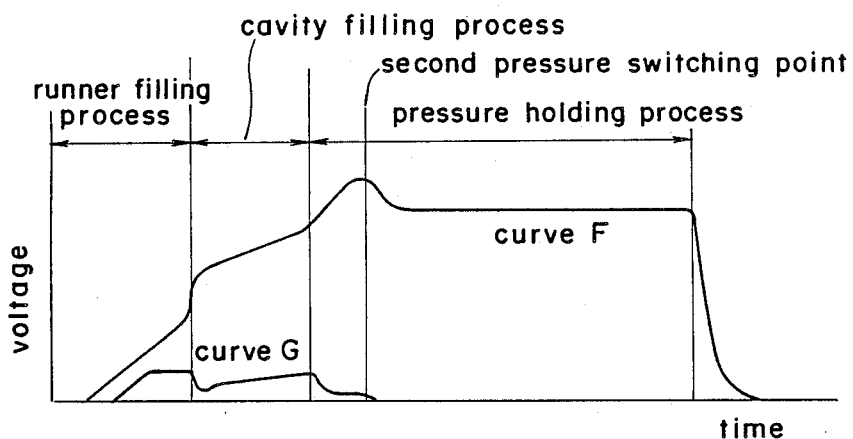
FIG. 4 is a chart showing the time lapse of the voltage to be caused by the pressure sensor during the molding operation in the construction of FIG. 3.

FIG. 4 shows one example of voltage over time caused by the pressure sensors 10, 21 of the arrangement of FIG. 1 during a molding operation. The voltage of the voltage sensor 10 is shown by the curve F, and voltage of the pressure sensor 21 is shown by the curve G. The pressure sensor 10 causes a voltage signal from the time when the melt front flows as far as the position A in FIG. 1. The pressure sensor 21 generates a voltage signal due to the force applied to the pressure receiving pin 11 from the time when the melt front comes as far as the position B. As the flow speed of the resin during the molding operation is almost constant along the runner 7, the increment of the pressure value per unit of time is almost constant. However, when the melt front comes to the point C of FIG. 1, a force is applied to the pressure receiving pin 12, and the rotation moment around the support point 18 is reversed since pressure is applied to both receiving pins 11, 12. As the distances from the support point 18 to each of pressure receiving pins 11, 12 is equal, equal increments of force are applied to both pressure receiving pins from the time when the melt front has passed the point C. As a result, the melt applies a constant force to the pressure sensor 21 after the melt front passes point C, and the voltage of the pressure sensor 21 remains constant at the same value.

After the resin has been filled into the runner, the resin passes through a narrow gate so that the pressure suddenly increases to reduce the amount of flow. As a result, the voltage value of the pressure sensor 10 suddenly rises, and the voltage value of the pressure sensor 21 lowers.

When the resin begins to be filled into the cavity, the pressure of the runner portion further increases. As the resin of the runner portion gradually increases a solid layer at this time from near the metal mold wall-face, the flow passage becomes narrower to increase the pressure loss so that the pressure difference between the pressure receiving pins 11, 12 becomes larger, and the voltage value of the pressure sensor 21 also increases gradually. After the resin is filled into the cavity, the flow of the resin suddenly decreases to reduce the voltage value of the pressure sensor 21 again. The voltage value of the pressure sensor 10 rises. However, the resin pressure to be injected from the nozzle lowers through a switching operation of valves (now shown) of a low pressure to another value setting (secondary pressure) as a pressure-retaining pressure, so that the voltage value of the pressure sensor 10 lowers with the secondary pressure switching point as a boundary.

Figure 5:
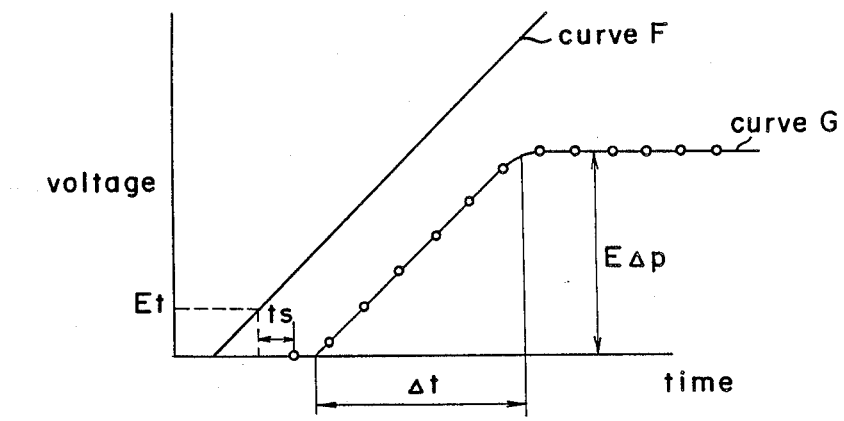
FIG. 5 is a chart showing the operation of the signal processing circuit of FIG. 3 when the signals to be shown in Fig. 4 have been caused.

FIG. 5 shows the operation in a case where the voltage profile shown in FIG. 4 has been obtained by the pressure sensors 10, 21 of the block diagram of FIG. 3. When the voltage from the pressure sensor 10 exceeds a set voltage Et, a short pulse voltage is generated by pulse generator 22 for each given time interval ts. The gate of the gate switch 24 opens the moment the pulse voltage is caused to feed to the A/D converter 25 the amplified value of the voltage from the pressure sensor 21. In this embodiment, the pressure sensor 21 responds to the converting means, the pulse generator 22, the gate switch 24, the A/D converter 25 responds to a sampling means, and the calculator 26 responds to calculating means.

Figure 6:
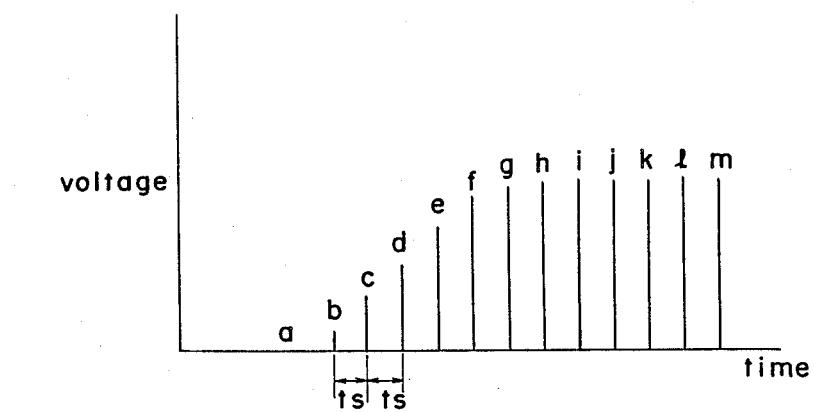
FIG. 6 is a chart showing the time lapse of the signals to be drawn into an A/D converter of FIG. 3 as the result of the signal processing shown in FIG. 5.

FIG. 6 shows the voltage values sampled to the A/D converter 25, provided for each time interval, reference character a showing a first sampling value, followed in order by b, c, d, e, f, g, h, i, j, k, l and m.

Here, the important value is $E_{\Delta p}$ representing temporarily a constant voltage value and a required time $\Delta t$ having been reached at $E_{\Delta p}$. Namely, $E_{\Delta p}$ is a voltage in accordance with the difference voltage between the two pressure-receiving pins, and $\Delta t$ is the time difference during which the resin has passed between such two points, as shown in FIG. 5.

The calculator 26 sequentially memorizes the digitalized voltage values fed from the A/D converter 25 and compares each value with the value fed last time. $E_{\Delta p}$ is determined through recognition that the same value or a constant-width value not zero has continued three times or more. The voltage increment per average unit of time from the value (the value b, c, d, e, f in FIG. 6) which is not contained in $E_{\Delta p}$ and is not zero is obtained, as shown in FIG. 5, the value provided through the division of $E_{\Delta p}$ by the voltage increment per unit time is obtained as $\Delta t$.

The difference pressure $\Delta p$ between the two pressure-receiving pins 11, 12 may be obtained through conversion of the value of $E_{\Delta p}$. Furthermore, the radius r of the runner and the distance l between the two pressure-receiving pins 11, 12 are fed in advance into the calculator to obtain the shearing speed $\dot{\gamma}$ and the viscosity $\eta$ by the following equations:

$$\text{viscosity } \eta = \frac{\Delta p \cdot \Delta t \cdot r^2}{8 \cdot l^2}$$

$$\text{shearing speed } \dot{\gamma} = \frac{4l}{r \cdot \Delta t}$$

The viscosity $\eta$ of the resin is expressed as a function of the shearing speed $\dot{\gamma}$ and the temperature T, and is shown by the equation:

$$\eta = \eta_0 \dot{\gamma}^{1-n} e^{\frac{C}{T}}$$

in the shearing speed region flowing into the metal molding mold. Here $\eta_O$ is reference viscosity, and n and C are constants peculiar to the resin. If three constants are provided in advance (which are measured by the use of a flow tester), the resin temperature T may be obtained through the provision of the viscosity $\eta$ and the shearing speed $\dot{\gamma}$. Also, the amount of flow may be obtained, from $\Delta t$, r and l, as $$Q = \frac{\pi r^2 l}{\Delta t}.$$

In the above-described first embodiment, the distances between the support point and the two points of force are equal, but in the present invention, the distances also may be unequal.

Figure 7:
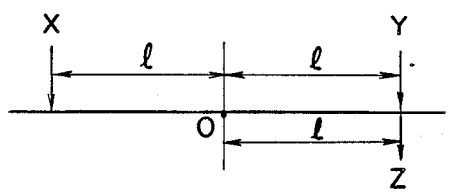
FIG. 7 is a chart showing the positional relation of a pressure receiving pin, a support point, and a pressure sensor in the construction of FIG. 1.

In FIG. 7, relating to the above first embodiment, the distance between the support point 0 and the upstream pressure receiving pin Y (or 11), the distance between the support point 0 and the downstream pressure receiving pin X (or 12), and the distance between the support point 0 and the pressure sensor Z (or 10) were respectively 1.

Figure 8:
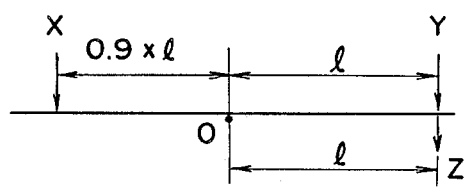
FIG. 8 is a chart showing the positional relation among the pressure receiving pin, the support point and the pressure sensor in accordance with a second embodiment.

FIG. 8 shows the positional relation in a second embodiment, wherein the distance between the downstream pressure receiving pin X and the support point O is 0.9×1, that is, 90% of the value of 1 of the distance between the support point O and the upstream pressure receiving pin Y and the distance between the support point O and the pressure sensor Z.

Figure 9:
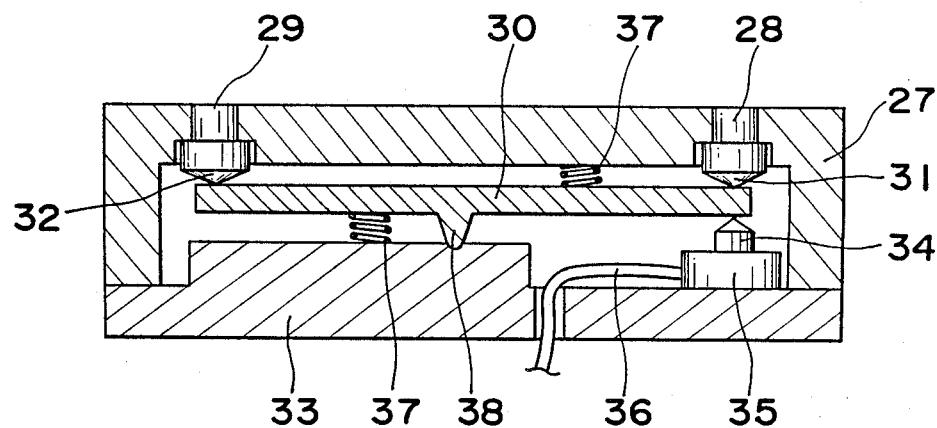
FIG. 9 is a cross-sectional view of a resin pressure means in accordance with the positional relation of FIG. 8.

FIG. 9 is a cross-sectional view of a resin pressure detecting means according to such second embodiment, where the upstream pressure-receiving pin 28 and the downstream pressure-receiving pin 29 have the same dimensions and are positioned within a case 27 in engagement with and supported by a plate 30. The tip ends of the pressure-receiving pins 28, 29 are conical members 31, 32 so that the positions of contact between plate 30 and the pressure-receiving pins 28, 29 will remain constant. A support 38 of the plate 30 is in contact against a bottom plate 33. Another pressure receiving pin 34 is provided at a position aligned with the pressure-receiving pin 28 and in contact with the opposite side of the plate 30 and is in contact with a pressure sensor 35. A cord or wire 36 extends from pressure sensor 35 for conveyance of signals therefrom. Springs 37 are provided for maintaining plate 30 in constant contact with the pressure sensor 35. The force of springs 37 is sufficiently weak as to not influence the detection sensitivity of the pressure sensor 35.

Figure 10:
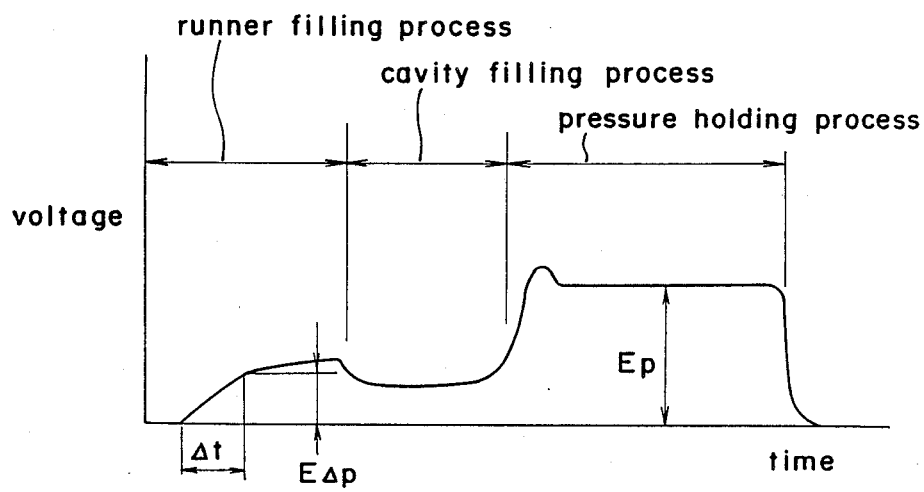
FIG. 10 is a chart showing the profile of the voltage to be caused in the pressure sensor in a case where the resin pressure detecting means of FIG. 9 has been engaged into the metal mold of FIG. 2.

FIG. 10 shows the lapse of time versus the voltage output from the pressure sensor 35 with the resin pressure detecting means of FIG. 9 employed with the metal mold shown in FIG. 2.

Force is applied to the pressure sensor 35 upon the application of pressure to the upstream pressure receiving pin 28. When the molten resin reaches the pressure receiving pin 29, a reverse force is applied to the lever formed by plate 30 about the support point 38 of the plate 30 as the center so that the time increment of the voltage from sensor 35 is reduced. As the distance from the support point 38 to the downstream pressure-receiving pin 29 is only 0.9 times the distance from the support point 38 to the upstream pressure-receiving pin 28, the force to be added to the pressure sensor 35 continues to increase by 10% of the time increment of the force previously applied to the upstream pressure-receiving pin. Accordingly, the voltage profile of the pressure sensor rises, first, at a sharp angle, and then rises at a shallow angle when the resin reaches the downstream pressure-receiving pin 29. Thus, the inflection point shows the voltage $E_{\Delta p}$ based on the difference voltage between the two points and the time difference $\Delta t$ of the time for flow between the two points. After filling of the runner, for the filling into the cavity, the flow first is restricted so that large pressure is applied both to the upstream pressure-receiving pin 28 and to the downstream pressure-receiving pin 29 to remove most of the pressure difference therebetween. The force to be applied upon the pressure sensor 35 at this time is one tenth of the force which is applied to the upstream pressure receiving pin 28. Namely, although the same force is applied to both pressure-receiving pins, 90% of the force applied to the upstream pressure receiving pin 28 is offset by the force applied to the downstream pressure-receiving 29. Only the remaining 10% is applied to the pressure sensor 35, because the force is applied in proportion to the distances between the support point of the lever and the respective pins. Accordingly, the voltage Ep to be caused by the pressure sensor 35 is the voltage equivalent to one tenth of the actual pressure.

Figure 11:
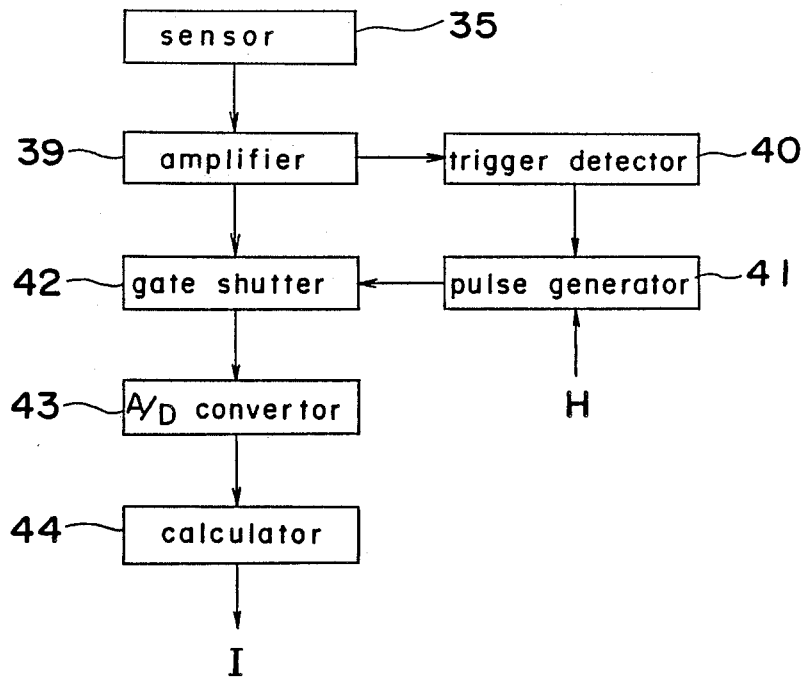
FIG. 11 is a block diagram of a signal processing circuit including a pressure sensor of FIG. 9.
Figure 12:
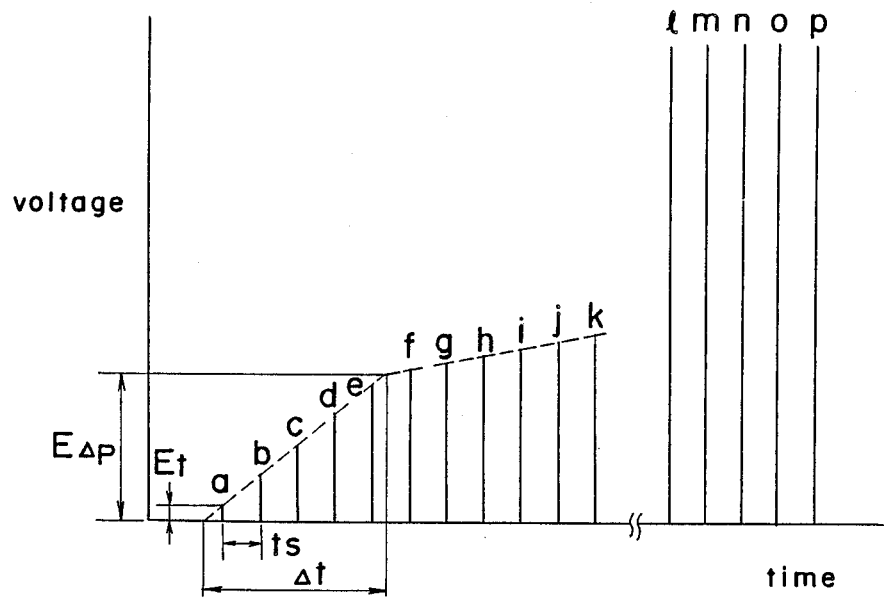
FIG. 12 is a chart showing the time lapse of the signal in a case where the voltage profile of FIG. 10 has been drawn into an A/D converter of the block diagram of FIG. 11.

FIG. 11 is a block diagram of a signal processing circuit including the pressure sensor 35 shown in FIG. 9. The voltage caused by the pressure sensor 35 is amplified by an amplifier 39, and such signal is fed to both a trigger detector 40 and a gate switch 42. The trigger detector 40 feeds the signal to a pulse generator 41 when the voltage of the signal to be fed from the amplifier 39 exceeds a trigger voltage. The pulse generator continues to produce short pulse signals at a given time interval after receiving the amplified signal, and stops pulse generation upon the application of a stop signal H from the exterior. The pulse signals are fed to the gate switch 42. The signal from the amplifier 39 is fed to an A/D converter 43 only when the pulse signals are supplied. FIG. 12 shows the time lapse of the signals fed from the A/D converter. The voltage signals from the amplifier 39 at a time interval as short as b, c, d . . . j, k for each of the given time intervals ts from the time point a when the trigger voltage Et has been reached are shown. At the time of flow restriction, the signals l, m, n, o, p equivalent to the restricted pressure are shown.

In the A/D converter 43, the signals b, c, d . . . and subsequent are digitalized and fed to a calculator 44. In the calculator 44, such signals are sequentially memorized, the last value and a new value are compared with each other to recognize the passage of inflection point $E_{\Delta p}$, because the difference between the two values has become a smaller value from a larger value, as shown in FIG. 12. The inflection point is obtained between the average straight-line increase pressure obtained from the values (the value of four points of b, c, d, e in the embodiment of FIG. 12) before the inflection point and the average straight-line increasing pressure obtained from the values (the values of f, g, h, i, j, k) after the inflection point. The voltage $E_{\Delta p}$ equivalent to the pressure difference between the two pressure receiving pins are read, the viscosity, the shearing speed, the temperature, and the quantity of flow may be obtained, as in the first embodiment, as the signal I, as show in FIG. 11.

Furthermore, this value is increased ten times (l, m, n, o, p in FIG. 12) at the point in time when of flow restriction occurs.

The relative distances between the support point and the pressure receiving pins and the pressure sensor may be selected as desired in accordance with the present invention. Also, the dispersion of the injection force may be freely selected by the combination of adjustment of the diameters of the pressure-receiving pins and the distances thereof from the support point. However, the pressure sensor requires the detection of the force in the direction of the rotation moment to which the pressure receiving pin on the side of the upper flow adds the force. They may be positioned respectively on the side opposite to the face against which the pressure receiving pin on the side of the upper flow comes into contact when the pressure sensor is brought into contact against the lever on the side of the upper flow, on the face against which the pressure receiving pin on the side of the lower flow comes into contact when the lever on the lower flow side is brought into contact against the pressure sensor.

Also, the resin pressure detecting means is not always required to be provided on the runner, and may be provided within the cavity. In such case, the cavity is generally plate-shaped, and the equations for obtaining the viscosity $\eta$, the shearing speed $\dot{\gamma}$ are slightly different from the equations in the above embodiment.

$$\text{viscosity } \eta = \frac{\Delta t \cdot \Delta p \cdot h^2}{12 l^2}$$

$$\text{shearing speed } \dot{\gamma} = \frac{6l}{\Delta t \cdot l}$$

wherein h is thickness, l is the interval between the pressure receiving pins, $\Delta t$ is time for flow between two points, and $\Delta p$ is the pressure difference between two points.

The following effects are provided by the method of the present invention.

(1) The difference in resin pressure between two points within the metal mold and the difference in time between the two points may be obtained with the use of one pressure sensor. Thus, the cost is reduced.

(2) As the measuring operation is performed with one pressure sensor, error is reduced. The difference in resin pressure between two points within the metal mold and the difference in time of flow between the two points may be obtained with high precision to obtain the viscosity, shearing speed, temperature, quantity of flow, and so on.

The second effect will be explained hereinafter. By detect the pressures at two places separately with the use of two pressure sensors, it is possible to obtain the pressure difference and time by comparison of the detected values. The time required for the resin to flow within the metal mold is extremely short, e.g. the short time required from the sprue entrance to the cavity end is 0.1 second or at the most is about 0.5 second. If the distance between two pressure-receiving pins is about 5 cm, the required flow time is from about 5 m.sec. to 500 m.sec.

When two pressure sensors are used, the sampling operation is required to be effected within the same time, and the difference in time required for the same pressure value is required to be detected. But, as it is extremely difficult to perform the sampling operation strictly within the same time, a highly efficient pulse oscillator of, for example, 10 through 100 kHz is further demanded. As a result, the entire circuit system is required to cope with such high frequency. Also, errors of calibration of two pressure sensors becomes a problem, that is, the percent of calibration error with respect to the pressure difference when the pressure difference has been obtained. Accordingly, higher precision is demanded.

On the other hand, high precision is provided, without such advanced technique as described hereinabove, with one pressure sensor.

Although the present invention has been fully described by way of example with reference to the accompanying drawings, it is to be noted here that various changes and modifications will be apparent to those skilled in the art. Therefore, unless otherwise such changes and modifications depart from the scope of the present invention, they should be construed as being included therein.

What is claimed is:

1. A method of monitoring a physical property of a resin during a process of molding said resin in a metal mold, said method comprising:
   supplying resin in a direction of flow through a flow passage in a metal mold;
   providing at respective upstream and downstream positions along said flow passage first and second pressure receiving members at opposite ends of a lever mounted at a pivot support between said ends outside of said flow passage;
   when the supplied resin reaches said upstream position, applying the force of said supplied resin to said first pressure receiving member to thereby cause said lever to pivot in a first direction about said pivot support;
   when said supplied resin reaches said downstream position, applying the force of said supplied resin to both said first and second pressure receiving members to thereby cause said lever to pivot in an opposite second direction about said pivot support; and
   determining, as a function of a difference in detected amounts of said pivoting of said lever in said first and second directions and of the time between said pivoting in said first and second directions, said physical property of said resin.

2. A method as claimed in claim 1, wherein said physical property comprises shearing speed or viscosity of said resin.

3. A method as claimed in claim 1, further comprising providing a pressure sensor to be responsive to said pivoting of said lever in said first and second directions, and detecting said amounts of pivoting in said first and second directions as a function of said lever acting on said pressure sensor.

4. A method as claimed in claim 3, comprising positioning said pressure sensor in alignment with said first pressure receiving member and on a side of said lever opposite aid first pressure receiving member.

5. A method as claimed in claim 1, comprising spacing said first and second pressure receiving members at equal distances from said pivot support.

6. A method as claimed in claim 1, comprising positioning said second pressure receiving member closer to said pivot support than said first pressure receiving member is to said pivot support.

* * * * *